US008297997B2

(12) United States Patent
Martens

(10) Patent No.: US 8,297,997 B2
(45) Date of Patent: Oct. 30, 2012

(54) CONNECTOR WITH A SURFACE WITH PRIMARY AND REDUNTANT CONNECTION POINTS

(75) Inventor: Hubert Cecile Francois Martens, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/126,361

(22) PCT Filed: Nov. 9, 2009

(86) PCT No.: PCT/IB2009/054959
§ 371 (c)(1),
(2), (4) Date: Apr. 27, 2011

(87) PCT Pub. No.: WO2010/055452
PCT Pub. Date: May 20, 2010

(65) Prior Publication Data
US 2011/0212651 A1    Sep. 1, 2011

(30) Foreign Application Priority Data

Nov. 11, 2008  (EP) .................................... 08168841

(51) Int. Cl.
*H01R 13/28*        (2006.01)

(52) U.S. Cl. ........................................................ 439/291
(58) Field of Classification Search .................. 439/660, 439/668, 289, 291, 843
See application file for complete search history.

(56) References Cited

U.S. PATENT DOCUMENTS

| 3,086,188 A | 4/1963 | Ross |
| 4,516,820 A * | 5/1985 | Kuzma .......................... 439/289 |
| 5,038,781 A | 8/1991 | Lynch |
| 5,176,528 A | 1/1993 | Fry |
| 5,692,917 A * | 12/1997 | Rieb et al. ..................... 439/225 |
| 6,183,316 B1 | 2/2001 | Morris |
| 6,250,967 B1 * | 6/2001 | Chu .............................. 439/668 |
| 2004/0106964 A1 | 6/2004 | Fischer |
| 2006/0135003 A1* | 6/2006 | Peloza .......................... 439/843 |
| 2007/0025809 A1 | 2/2007 | Lee |

* cited by examiner

*Primary Examiner* — Chandrika Prasad

(57) ABSTRACT

A connector (10, 30, 40) is provided for coupling an electronic circuit (11) of an electronic device to sensor and/or actuation elements (12) of the electronic device. The connector (10, 30, 40) comprises at least one connection surface (21) with i connection points (13), the i connection points (13) comprise j primary connection points (13) for coupling the electronic circuit (11) to j corresponding ones of the elements (12), and k redundant connection points (13) for redundantly coupling the electronic circuit (11) to at least one of the elements (12). The primary and the redundant connection points (13) for the at least one of the elements (12) are distributed over the connection surface (21).

20 Claims, 3 Drawing Sheets

CONNECTOR WITH A SURFACE WITH PRIMARY AND REDUNTANT CONNECTION POINTS

FIELD OF THE INVENTION

This invention relates to a connector for coupling an electronic circuit of an electronic device to sensor and/or actuation elements of the electronic device, the connector comprising a connection surface with connection points being arranged for coupling the electronic circuit to corresponding ones of the elements.

BACKGROUND OF THE INVENTION

Many electronic devices comprise a number of sensing and/or actuation elements for interacting with their environment. In such devices, an electronic circuit is coupled to the different elements. For easy replacement of either the electronic circuit, or the sensing/actuating parts of the electronic device, it may be preferable to provide the electronic device in the form of a first unit comprising the electronic circuit and a separate second unit comprising the elements. A connector should be provided for coupling the first unit and the second unit. If the electronic device comprises many sensing/actuating elements and the connector is frequently disconnected and reconnected, some of the connections may fail. Such connection failures may arise from, e.g., mechanical damage or contaminated connection points. Especially for electronic devices with a medical function, e.g. EEG, ECG or EMG devices, such connection failures may have undesired and even harmful consequences.

For example, many implanted medical devices contain a variety of sensor (e.g. biosensor, or recording electrode) and/or actuation elements (e.g. stimulation electrodes). The sensor and/or actuation elements are implanted in the patient's body, e.g. in brain tissue. Electronic circuits are needed for the read out of the sensor elements and the activation of the actuation elements. Preferably, the electronics are contained in a container which is separated from the carrier of the sensing or actuating elements. As the electronics may fail or have a limited lifetime it is often desirable to be able to connect or disconnect the electronics and sensor or actuation elements. A known example of this is a neuro stimulator implant consisting of an implanted pulse-generator (IPG) unit that contains the battery and electronics and via a biomedical connector and lead-wire is physically and electrically connected to the actuating electrodes that are implanted in the brain tissue.

For assuring proper functioning of the implantable medical device the connector should be reliably and repeatedly connected, disconnected and reconnected to a unit comprising the electronic circuit, e.g. for replacement or revision purposes. Connection and reconnection usually occurs under surgical conditions. E.g. blood, body fluids, tissue debris or other materials may contaminate the connector surface. Also the cleaning or drying agents used such as cotton or other materials such as dental cement, bone cement, glue etc, may lead to contamination of the connector surface. As a result part of the physical or electronic connections between the electronics and sensor or actuation elements becomes obscured. This may eventually lead to (partial) device failure, e.g. because not all sensor or actuation elements can be addressed by the electronics unit.

OBJECT OF THE INVENTION

It is an object of the invention to provide a connector as described in the opening paragraph, which connector allows for reliably and repeatedly connecting the electronic circuit to the sensor and/or the actuation elements.

SUMMARY OF THE INVENTION

According to a first aspect of the invention, this object is achieved by providing a connector for coupling an electronic circuit of an electronic device to sensor and/or actuation elements of the electronic device, the connector comprising at least one connection surface with i connection points, the i connection points comprising j primary connection points for coupling the electronic circuit to j corresponding ones of the elements and k redundant connection points for redundantly coupling the electronic circuit to at least one of the elements, the primary and the redundant connection points for the at least one of the elements being distributed over the connection surface.

In this way a connector is provided which is robust to partial contamination or mechanical failure of the surfaces or the connection points of the connector and/or counter-connector. A larger number of connection points is provided for at the connection surface than the number of sensor or actuation elements that need to be connected to the electronic circuit. For example, n times (n=2, 3, 4, etc) more connector points are provided for than the number of sensor or actuation elements. If one connection point becomes unusable, e.g. because of contamination, at least one of the redundant connection points may still be usable and the element will still be coupled to the electronics. It is to be noted that the primary connection points and the redundant connection points may be identical. The distinction between primary and redundant points is more for descriptive purposes than for technical ones. Any one of the connection leading to one element may be considered the primary one. All other ones are then considered redundant.

Preferably, the redundancy is distributed over the connection surface in order to decrease the chance of all redundant connection points for one element being contaminated at once, e.g. by one spot of blood. For example, the primary connection point for coupling to one of the elements and at least one redundant connection point for coupling to the same one of the elements are physically separated by at least one connection point for coupling to another one of the elements. By providing redundant connection points for coupling to an element at some distance from each other, the chance of all connections to one element failing because of, e.g., contamination is significantly reduced. When the distance between the redundant connection points is further increased, the reliability of the connector is further improved. The distance between connection points may be increased by using a larger distance between adjacent connection points and/or by putting more connection points in between two connection points for the same element.

In a preferred embodiment of the connector according to the invention, a number of redundant connection points per element differs for different elements. In this embodiment, the reliability of the most important functions of the device may be improved. If during the connecting or reconnecting of the electronic circuit some connections to the more important elements are not established as intended, plenty of redundant connections are available for taking over the tasks of the missing connection. By improving the reliability of the more important functions, the adverse effects of connection problems are minimized. Assigning additional connections points to the more important elements may decrease the reliability of the less important one. However, failure of the less important elements will be less problematic and, if the electronic device is a medical device, will cause less health risks for the patient.

A similar effect is provided by providing a connector wherein a distance between two connection points for coupling the electronic circuit to the more important element is larger than a distance between two connection points for coupling the electronic circuit to the less important element. Again the reliability of the more important functions is increased more than the reliability of the less important ones. Distance may be measured in millimeters or micrometers or in a number of other connection points in between one connection point and another connection point for the same element. It is to be noted that importance is a relative term. What is important for one user or patient may be less important for another. So preferably, in the above two mentioned embodiments, there is provided a possibility for the user/doctor/surgeon to assign redundant connection points to specific elements.

The sensor and/or actuation elements of an implantable medical device may be active at different parts of the patient's body. For example, a deep brain stimulating device may use multiple groups of stimulating electrodes at several locations in the brain. Preferably, geometrical relations of the elements in the patient's body are not transferred to the connection surface. Connection points and redundant connection points for adjacent elements are preferably separated at the connection surface. Thereby it is ensured that contamination of multiple adjacent connection points does not immediately result in failure of the implanted medical device at a larger area in the patient's body. Instead, contamination of adjacent connection points will only result in slightly reduced functionality spread over the complete active area of the device. These and other aspects of the invention are apparent from and will be elucidated with reference to the embodiments described hereinafter.

DETAILED DESCRIPTION OF THE INVENTION

Figure 1:
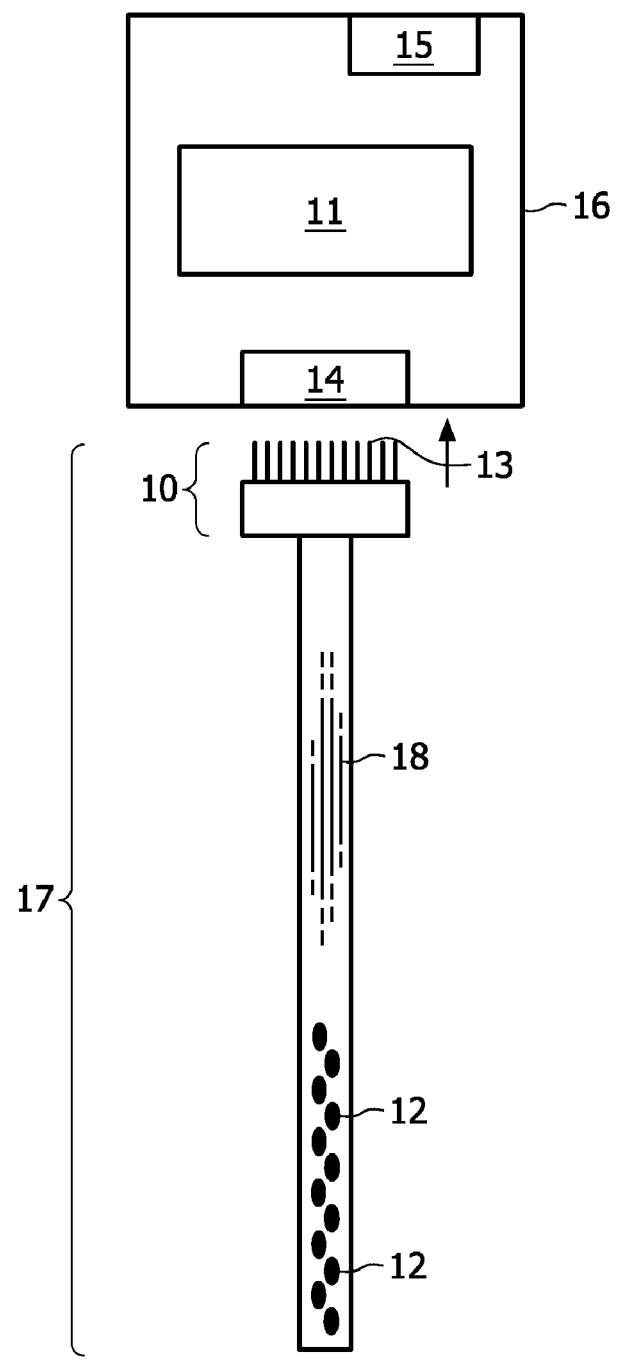
FIG. 1 schematically shows an implantable medical device and a connector according to the invention.

FIG. 1 schematically shows an implantable medical device and a connector 10 according to the invention. The examples shown in this detailed description mainly show an implantable medical device. It is however to be noted that the shown embodiments are provided as an example only and that the features described are also applicable to other types of electronic devices using a connector for reliably coupling multiple elements to an electronic circuit. The electronic device may, e.g. be a neuro-stimulator implant, a cardiac stimulator or an ECG, EMG or EEG monitoring device. In the implantable medical device, sensor and actuation elements 12 may both be used for providing a medical device that can selectively stimulate physical activity in dependence of locally monitored physical values. The medical device comprises an operational unit 17 and a support unit 16. The operational unit 17 comprises multiple sensor or actuation elements 12. In this example, the elements 12 are arranged close together in an array-like manner. Alternatively, depending on the function of the implantable device, the elements 12 may (partly) be separate elements 12 which may be spread over a larger area of the patient's body. The support unit 16 comprises an electronic circuit 11 for operating the medical device. The electronic circuit 11 may receive and process signals from the monitoring elements 12 and/or may generate pulses for the actuation elements 12 to stimulate, e.g., selected nerve cells or muscle fibers. The electronic circuit 11 may further comprise some memory for storing e.g. personal, operational or monitored parameters. Monitored parameters may be used to control the functioning of the device or may be sent to an external receiver, using an optional data transmission unit (not shown). A data receiver (not shown) may be included for receiving, e.g., operational instructions. A battery 15 may be provided for powering the electronic circuit 11.

Preferably, the support unit 16 is implanted just below the patient's skin. When the medical device is implanted, a connector 10 of the operational unit 17 is engaged with a counter connector 14 of the support unit 16. The connector 10 comprises a number of connection points 13 for connecting to corresponding connection points on the counter connector 14. The connection may be established by sliding pins 13 of the connector 10 into holes of the counter connector 14, by pushing conductive areas against each other or in any other conventional way used for electronic connectors. Because the sensor and/or actuation elements 12 may be operative deeper inside the body, a bundle of wires 18 couples the connection points 13 in the connector 10 to the sensor and/or actuation elements 12. The wires 18 are arranged and connected in such a way that at least part of the elements 12, are coupled to multiple connection points 13 on the connector 10. By providing redundant connections, the reliability of the connection between the support unit 16 and the operational unit 17 is increased as will be described in more detail below with reference to FIG. 2.

Figure 2:
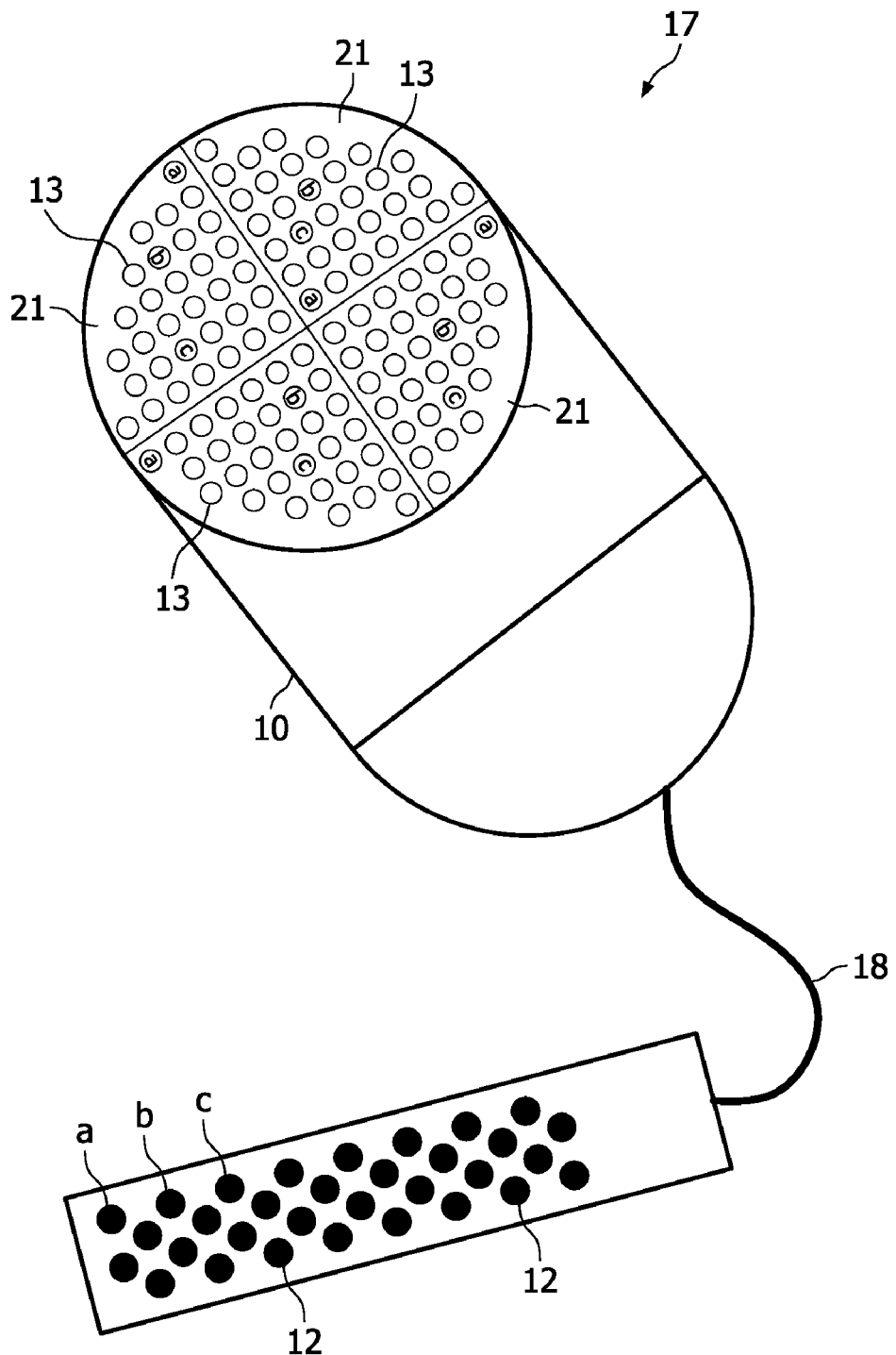
FIG. 2 shows a connector and some sensor/actuation elements according to the invention.

FIG. 2 shows an operational unit 17 with a connector 10 and a set of sensor and/or monitoring elements 12. Like in FIG. 1, the elements 12 are arranged in an array-like manner. Three adjacent elements a, b and c have been identified explicitly. The wires 18 coming from the elements 12 are bundled and lead to the connector 10. In the connector 10, the wires 18 are coupled to the connection points 13 at the connection surface 21. The connector 10 comprises more connection points 13 than elements 12. Each active element 12 should be connected to at least one of the connection points 13. Via the connection points 13 and the counter connector 14, the elements 12 are coupled to the electronic circuit 11. The electronic circuit 11 may provide pulses for the actuation elements 12 and may receive signals from the monitoring elements 12. A suitably configured electronic circuit 11 may make it possible to use one element 12 for sensing as well as for actuating.

When each element 12 is connected to one connection point 13, the remaining connection points 13 would be redundant. According to the invention these redundant connection points 13 are used for making additional/backup connections to the elements 12. In this way a biomedical connector 10 is provided which is robust to partial contamination of the surfaces 21 of the connector 10 and/or counter-connector 14. If one connection fails, a backup connection may still be available somewhere else on the connection surface 21 for coupling the element 12 to the electronic circuit 11. A larger number of connector points 13 is provided for than the number of sensor or actuation elements 12 that need to be connected to the electronic circuit 11. For example, n times (n=2, 3, 4, etc) more connector points 13 are provided for than the number of sensor or actuation elements 12.

Preferably, the redundancy is distributed over the connection surface 21 in order to decrease the chance of all redundant connection points 13 for one element 12 being contaminated at once, e.g. by one spot of blood. An exemplary way of distributing the redundancy is shown in FIG. 2. Elements a, b and c all have four different connection points 13 for coupling to the electronic circuit 11. Each one of the four connection points 13 lies in another quadrant of the connection surface 21. It is to be noted that it does not matter which one of the four connection points 12 is considered the 'normal' connection point 13 and which ones are considered redundant connection points 13.

The electronic circuit 11 may decide to use all four connections to an element 12 or may be configured to use only one of the available connection points 13, e.g., by closing a switch to the other connection points 13 for the same element 12. The electronic circuit 11 may check the integrity of single connection points 13 by monitoring an impedance from the electronic circuit 11 through the connection point 13 to one of the elements 12. When a connection point 13 fails, the electronic circuit 11 may decide not to use it anymore.

All connection points 13 for one element 12 are preferably situated far away from each other. The larger the distance between two connection points 13, the larger the chance that one connection point 13 will still function properly when the other one malfunctions due to contamination. Preferably, the connection surface 21 is designed in such a way that for most elements different connection points 13 are available at a minimal distance of at least one quarter of a width of the connection surface 21. By providing redundant connection points 13 for coupling to an element 12 at such a distance from each other, the chance of connections failing because of, e.g., contamination is significantly reduced. When the distance between the redundant connection points 13 is further increased, e.g. to one third or half of the width of the connection surface 21, the reliability of the connector 10 is further improved.

In a preferred embodiment of the connector 10 according to the invention, the elements 12 comprise a more important element 12 and a less important element 12 and a number of redundant connection points 13 per element 12 is higher for the more important element 12 than for the less important element 12. In this embodiment, the most important functions of the medical device are the most reliable. If during the connecting or reconnecting of the electronic circuit 11 some connections to the more important elements 12 are not established as intended, plenty of redundant connections are available for taking over the tasks of the missing connection. By improving the reliability of the more important functions, the adverse effects of connection problems on the health of the patient are minimized. Assigning additional connections points 13 to the more important elements 12 may decrease the reliability of the less important one, but failure of the less important elements 12 will be less problematic and will cause less health risks for the patient.

A similar effect is provided by providing a connector 10 wherein a distance between two connection points 13 for coupling the electronic circuit to the more important element 12 is larger than a distance between two connection points 13 for coupling the electronic circuit to the less important element. Again the reliability of the more important functions is increased more than the reliability of the less important ones. It is to be noted that importance is a relative term. What is important for one patient may be less important for another patient. So preferably, there is provided a possibility for the user/doctor/surgeon to assign redundant connection points to specific elements.

Figure 3:
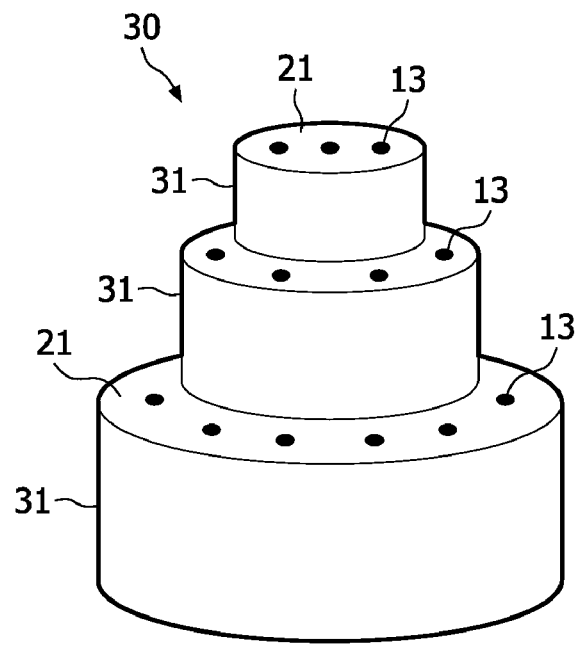
FIG. 3 shows a connector with multiple plateaus.

The sensor and/or actuation elements 12 of the implantable medical device 10 may be active at different parts of the patient's body. For example, a deep brain stimulating device may use multiple groups of stimulating electrodes 12 at several locations in the brain. Preferably, geometrical relations of the elements 12 in the patient's body are not transferred to the connection surface. Connection points 13 and redundant connection points 13 for adjacent elements 12 are preferably separated at the connection surface. Thereby it is ensured that contamination of multiple adjacent connection points 13 does not immediately result in failure of the implanted medical device at a larger area in the patient's body. Instead, contamination of adjacent connection points 13 will only result in slightly reduced functionality spread over the complete active area of the device FIG. 3 shows a connector 30 with multiple plateaus 31. This connector 30 comprises three stacked plateaus 31 with connection surfaces 21. On each connection surface 21 some connection points 13 are provided. It is an advantage of this connector 30, that the three connection surfaces 21 are somewhat separated and contamination of one of the surfaces 21 may not immediately spread to the other surfaces. Preferably, a sensor or actuation element 12 of the implantable medical device, is coupled to connection points 13 on different plateaus 31.

Figure 4:
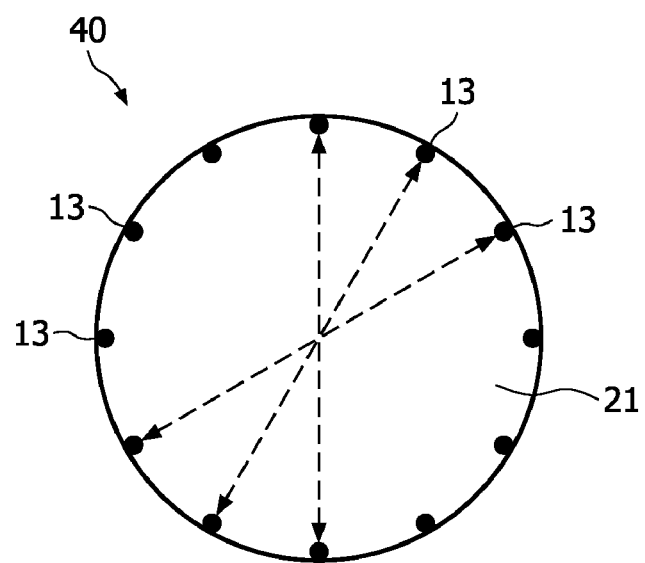
FIG. 4 shows an alternative arrangement of connection points on a connection surface.

FIG. 4 shows an alternative arrangement of connection points 13 on a connection surface 21. Here, the connection points 13 are arranged at the circumference of a circular surface 21. By placing redundant connection points 13 for one element 12 at positions opposite to each other (seer arrows), the distance between the different connection points 13 for one element 12 is optimized.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A connector for coupling an electronic circuit of an electronic device to sensor and/or actuation elements of the electronic device, the connector comprising at least one connection surface with i connection points, the i connection points comprising:
   j primary connection points for coupling the electronic circuit to j corresponding ones of the elements, and
   k redundant connection points for redundantly coupling the electronic circuit to at least one of the elements,
   the primary and the redundant connection points for the at least one of the elements being distributed over the connection surface.

2. A connector as claimed in claim 1, wherein the primary connection point for coupling to one of the elements and at least one redundant connection point for coupling to the same one of the elements are physically separated by at least one connection point for coupling to another one of the elements.

3. A connector as claimed in claim 2, wherein the primary connection point for coupling to one of the elements and at least one redundant connection point for coupling to the same one of the elements are physically separated by at least two connection points for coupling to another one of the elements.

4. A connector as claimed in claim 1, wherein a number of redundant connection points per element differs for different elements.

5. A connector as claimed in claim 4, wherein the elements comprise a more important element and a less important element and wherein the number of redundant connection points per element is higher for the more important element than for the less important element.

6. A connector as claimed in claim 1, wherein the elements comprise a more important element and a less important element and wherein a distance between two connection points for coupling the electronic circuit to the more important element is larger than a distance between two connection points for coupling the electronic circuit to the less important element.

7. A connector as claimed in claim 1, comprising at least one additional connection surface, the primary connection point for coupling to one of the elements being provided at the connection surface and at least one redundant connection point for coupling to the same one of the elements being provided at the additional connection surface.

8. A connector as claimed in claim 1, the connection points being provided at a circumference of the connection surface.

9. A connector as claimed in claim 8, wherein the primary connection point for coupling to one of the elements and at least one redundant connection point for coupling to the same one of the elements are provided at opposite positions at the circumference of the connection surface.

10. A connector as claimed in claim 1, wherein the connector is arranged for coupling the electronic circuit of an implantable medical device to implanted sensor and/or actuation elements of the implantable medical device.

11. A connector as claimed in claim 10, wherein the connection points for coupling the electronic circuit to two adjacently implanted elements are not provided adjacently on the connection surface.

12. The connector of claim 1, wherein j>2 and k>2.

13. The connector of claim 1, where for each of the redundant connection points is connected to one of the primary connection points.

14. The operational unit of claim 13, wherein the primary connection point and at least one redundant connection point are provided at opposite positions at a circumference of the connection surface.

15. The operational unit of claim 13, wherein there are at least two connection surfaces, wherein at least a first one of the connection surfaces is stacked on a second one of the connection surfaces to define two plateaus at two different levels, and wherein primary connection point is provided at the first one of the connection surfaces, and the redundant connection point is provided at the second one of the connection surfaces.

16. An operational unit, comprising:
 a plurality of sensor and/or actuation elements;
 a connector configured to connect the elements to an electronic circuit of an electronic device, wherein the connector has at least one connection surface and a plurality of connection points provided at the at least one connection surface; and
 a plurality of wires each electrically connecting one of the elements to at least one of the connection points,
 wherein the wires electrically connect at least a first one of the elements to at least two of the connection points including a primary connection point and at least one redundant connection point.

17. The operational unit of claim 16, wherein the wires electrically connect the first one of the elements to exactly N connection points, and wherein the wires electrically connect a second one of the elements to exactly M connection points, where M and N are integers greater than two, and wherein M>N.

18. The operational unit of claim 16, wherein the at least two connection points electrically connected to the first one of the elements includes the primary connection point and at least two redundant connection points.

19. The operational unit of claim 16, wherein each of the at least two connection points electrically connected to the first one of the elements are separated from each other by at least one other connection point.

20. The operational unit of claim 16, wherein there are j elements and m connection points, and wherein $m=j*x$, where x is an integer $\geq 2$.

* * * * *